(12) United States Patent
LeDonne et al.

(10) Patent No.: US 9,656,441 B2
(45) Date of Patent: May 23, 2017

(54) TRANSDERMAL PATCH

(71) Applicant: ALFRED E. TIEFENBACHER (GmbH & CO. KG), Hamburg (DE)

(72) Inventors: John LeDonne, Ridgewood, NJ (US); Claudia Meyer, Winsen-Stoeckte (DE)

(73) Assignee: ALFRED E. TIEFENBACHER ( GMBH & CO. KG), Hamburg (DE)

( * ) Notice: Subject to any disclaimer, the term of this patent is extended or adjusted under 35 U.S.C. 154(b) by 0 days.

(21) Appl. No.: 14/592,712

(22) Filed: Jan. 8, 2015

(65) Prior Publication Data

US 2016/0199313 A1  Jul. 14, 2016

(51) Int. Cl.

| | |
|---|---|
| *A61K 9/70* | (2006.01) |
| *A61L 15/16* | (2006.01) |
| *A61M 35/00* | (2006.01) |
| *A61F 13/02* | (2006.01) |
| *B32B 37/00* | (2006.01) |
| *A61K 38/00* | (2006.01) |
| *B32B 7/12* | (2006.01) |
| *A61K 31/485* | (2006.01) |
| *A61K 47/32* | (2006.01) |
| *B32B 5/02* | (2006.01) |

(52) U.S. Cl.
CPC .............. *B32B 7/12* (2013.01); *A61K 9/7084* (2013.01); *A61K 31/485* (2013.01); *A61K 47/32* (2013.01); *B32B 5/022* (2013.01); *B32B 5/024* (2013.01); *B32B 2262/0284* (2013.01); *B32B 2307/51* (2013.01); *B32B 2556/00* (2013.01)

(58) Field of Classification Search
None
See application file for complete search history.

(56) References Cited

U.S. PATENT DOCUMENTS

| | | | |
|---|---|---|---|
| 2005/0118247 A1* | 6/2005 | Cordes | A61K 9/7061 424/449 |
| 2011/0104215 A1* | 5/2011 | Ito | A61K 9/7061 424/400 |

FOREIGN PATENT DOCUMENTS

| | | |
|---|---|---|
| EP | 0430019 A2 | 6/1991 |
| EP | 0 535 111 A1 | 4/1993 |
| EP | 1009393 A2 | 6/2000 |
| EP | 2 272 507 A1 | 1/2011 |
| WO | WO 96/19975 A1 | 7/1996 |
| WO | WO 98/36728 A2 | 8/1998 |
| WO | WO 2012/065740 A1 | 5/2012 |

OTHER PUBLICATIONS

Pastore et al.; British Journal of Pharmacology (2015) 172; pp. 2179-2209.*
Wilson et al.; "Three Generations: The Past, Present, and Future of Transdermal Drug Delivery Systems," May 16, 2011; pp. 1-22.*

(Continued)

*Primary Examiner* — Jeffrey T Palenik
(74) *Attorney, Agent, or Firm* — Birch, Stewart, Kolasch & Birch, LLP

(57) ABSTRACT

A transdermal patch includes a protective layer, a matrix layer, an adhesive layer, and a cover layer. The cover layer is at least partially bi-elastic, and the adhesive layer comprises an acrylic copolymer having hydroxyl functional groups. The matrix layer comprises a physiologically effective amount of buprenorphine or pharmaceutically acceptable salts thereof.

17 Claims, 1 Drawing Sheet

(56) References Cited

OTHER PUBLICATIONS

FDA approved label of Butrans (buprenorphine) Transdermal System for transdermal administration. Initial approval 1981, revised Jun. 2014.
NORSPAN approved label, Mar. 2009, with English language translation.
Transtec PRO approved label, Aug. 2012, with English language translation.

* cited by examiner

TRANSDERMAL PATCH

BACKGROUND OF THE INVENTION

1. Field of the Invention

The present invention relates to a transdermal patch, a preparation of a transdermal patch, and a use of the transdermal patch. In particular, the transdermal patch comprises buprenorphine as an active agent.

2. Description of Background Art

Buprenorphine is an endoethylene morphinan derivative and a partial agonist of μ-opioid receptors with a strong analgesic effect. For parenteral administration, the action of 0.3 mg of buprenorphine corresponds to the effect of 12 mg morphine. The duration of action is about 6-8 hours, which is about twice as long as comparable strong analgesics. Because of its dependence potential, buprenorphine should not be used to treat acute pain.

As a transdermal patch, sustained release buprenorphine is used especially for the treatment of moderate non-malignant pain in various potencies if an opioid to achieve adequate analgesia is necessary (e.g. Norspan® 5/10/20 micrograms/hour transdermal patch) or for the treatment of moderate to severe pain, such as that associated with cancer, and severe pain when there is insufficient efficacy with non-opioid analgesics (such as with Transtec PRO® 35/52.5/70 micrograms/hour transdermal patch) or for the management of pain severe enough to require daily, around-the-clock, long-term opioid treatment for which alternative treatment options are inadequate (e.g. Butrans® 5/10/15/20 micrograms/hour transdermal system).

Since these transdermal opioid patches are applied over a period of up to 7 days on the skin, transdermal therapeutic system (e.g., a patch) must enable consistent drug release over this period, must be comfortable to the wearer, and have sufficient adhesive force so that the matrix layer does not detach from the cover layer and the patch does not dissociate from the skin prematurely.

Transdermal patches comprising buprenorphine, which are already available on the market have a unidirectional cover layer of polyethylene terephthalate that faces away from the skin of the wearer (see EP 1009393 B1 and Norspan® 5/10/20 micrograms/h (manufactured by Gruenenthal) and Transtec PRO® 35/52.5/70 micrograms/h (manufactured by Gruenenthal)). However, there is still a need to improve the comfort of the patch and to provide a transdermal therapeutic system that has a sufficient adhesion of the drug-containing matrix during the storage period and in use.

SUMMARY OF THE INVENTION

In a first embodiment the present invention is directed to a transdermal patch comprising a protective layer, a matrix layer, an adhesive layer, and a cover layer. The cover layer is at least partially bi-elastic and the adhesive layer comprises an acrylic copolymer having hydroxyl functional groups. The matrix layer comprises a physiologically effective amount of an active drug, such as buprenorphine. The matrix layer may be arranged so as to be in contact with the protective layer and in contact with the adhesive layer but not in contact with the cover layer. The adhesive layer may be arranged to be in contact with the cover layer and may be optionally in contact with the protective layer. A separating layer is optionally between the matrix layer and the adhesive layer. The cover layer should have an elasticity in the longitudinal and transverse direction of 20% or more. The acrylic copolymer having hydroxyl functional groups may be crosslinked. The acrylic copolymer may comprise a combination of 2-ethylhexyl acrylate, glycidyl methacrylate, 2-hydroxyethyl acrylate, and vinyl acetate. The acrylic copolymer may also comprise a combination of 2-ethylhexyl acrylate, 2-hydroxyethyl acrylate, and vinyl acetate. The adhesive layer should not contain the active drug, such as buprenorphine.

In a second embodiment the present invention is directed to process for preparing the transdermal patch described above, which comprises:

providing an active drug composition, which contains the active drug, e.g. buprenorphine, and producing matrix layer therefrom, which contains the active drug, providing a composition comprising an acrylic copolymer having hydroxyl functional groups for producing an adhesive layer, providing a protective layer, providing a bi-elastic cover layer, and combining the above listed components in the layer order described above to produce a transdermal patch according to the present invention.

Alternatively, the transdermal patch of the present invention may be produced in accordance with the following process:

producing a laminate comprising a matrix layer which contains the active drug, such as buprenorphine and a protective layer, preparing a laminate comprising an adhesive layer, which includes an acrylic copolymer having hydroxyl functional groups, and a cover layer, connecting the two laminates to produce the transdermal patch.

A top surface of the buprenorphine-containing matrix layer may be covered with a separating layer. In addition, the laminate with the adhesive layer may also have an interim protective layer on the surface of the adhesive layer, which may be removed from the laminate before connecting the laminate with the laminate comprising the matrix layer. The process may further comprise cutting the transdermal patch into single doses.

A third embodiment of the present invention relates to a use of a transdermal patch for the treatment, alleviation, and/or prophylaxis of pain.

A fourth embodiment of the present invention is directed to a method for the treatment, alleviation, and/or prophylaxis of pain by administering a transdermal patch according to the present invention to a patient in need thereof.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to one of ordinary skill in the art from this detailed description.

BRIEF DESCRIPTION OF THE DRAWINGS

The present invention will become more fully understood from the detailed description given below and the accompanying drawings that are given by way of illustration only and are thus not limitative of the present invention.

DETAILED DESCRIPTION OF THE INVENTION

The present invention will now be described with reference to the accompanying drawings.

The present invention is directed to a transdermal patch.

Figure 1:
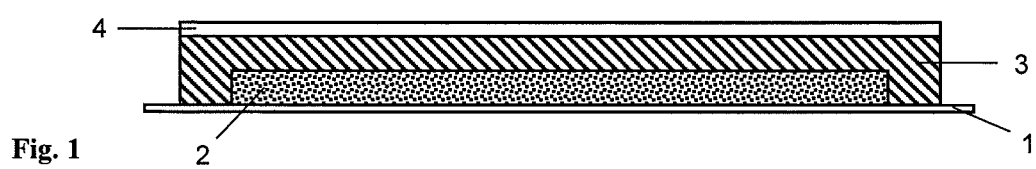
FIG. 1 is a schematic cross-sectional view of a transdermal therapeutic system of the present invention with a protective layer 1, a matrix layer 2, an adhesive layer 3, and a cover layer 4.

FIG. 1 is an example of a transdermal patch of the invention. A cover layer 4 is present on the side of the transdermal patch that does not contact the skin of the user. The transdermal patch according to the present invention allows for improved comfort during bodily movements due to the bi-elastic cover layer 4. A protective layer 1 is present on the opposite side of the transdermal patch from the cover layer 4. A matrix layer 2, which contains a drug, is on top of the protective layer 1. The drug in the matrix layer 2 is preferably buprenorphine. An adhesive layer 3 is present on the sides and above the matrix layer 2 between the cover layer 4 and the protective layer 1.

In the present invention, the bi-elastic cover layer 4 in an unstretched condition has elasticity or stretchability in the longitudinal direction (lengthwise) of more than 20% and has elasticity transversely to the longitudinal direction (transverse) of more than 20%. The longitudinal extensibility is preferably greater than or equal to 25%, more preferably 30% to 70%, and most preferably 40% to 60%. The extensibility in the transverse direction is preferably greater than or equal to 25%, more preferably greater than or equal to 30%, even more preferably greater than or equal to 35%, and most preferably greater than or equal to 40%. In a particularly preferred embodiment, extensibility in the longitudinal direction is 40% to 60%, and the extensibility in the transverse direction is 35%. The elasticity or extensibility is determined according to DIN 61632 (December 2009).

As the cover layer 4 of the transdermal patch, any material that is typically used for a cover layer of a transdermal patch may be used. However, the material may preferably be a woven fabric or a non-woven fabric. The cover layer 4 may also comprise one or more of polypropylene, polyamide, rayon, and polyester. A preferred cover layer 4 is a bi-elastic polyester fabric, which is available, for example, from Karl Otto Braun KG (KOB), Wolfenstein, Germany.

The protective layer 1 is present on the opposite side of the transdermal patch from the cover layer 4 and is to be removed before applying the patch to a user's skin. As the protective layer 1 of the transdermal patch, any material that is typically used for a protective layer of a transdermal patch may be used. However, the material may preferably be a film. The protective layer 1 may also comprise one or more of polyester (e.g., PET), polypropylene, polyvinylchloride, high density polyethylene (HDPE), aluminum, and paper. The protective layer 1 may be impermeable to the drug but also easy to detach from the matrix layer 2 and the adhesive layer 3. The protective layer 1 may be treated with one or more of silicone, fluorosilicone, fluorocarbon (e.g., polytetrafluoroethylene), and polyethylene. Preferably, the protective layer 1 may be made of siliconized PET or fluoropolymer-coated PET. Commercially available products to use as the protective layer 1 include Primeliner® FL2000 PET 100 microns 1S or Primeliner® SN 410/140 (manufactured by Loparex (Apeldoorn, Netherlands)) or Scotchpak 1022 (manufactured by 3M (St. Paul, Minn., USA)) or Grade 29058 D3.0 Clear PETxX5000A/000 (manufactured by Loparex (Iowa City, Iowa, USA)). The thickness of the protective layer 1 may be 50 to 120 microns as measured according to ISO 534. The protective layer 1 may also be transparent.

A matrix layer 2, which contains a drug, is on top of the protective layer 1. Preferably, the matrix layer 2 is directly on top of the protective layer 1. The drug in the matrix layer 2 may preferably be a buprenorphine free base and/or a pharmaceutically acceptable salt thereof. The drug in the matrix layer 2 is more preferably the buprenorphine free base. The term "buprenorphine" includes all usable embodiments of buprenorphine. The matrix layer may also include oleyl oleate, povidone K90, levulinic acid, crosslinked poly[acrylic acid-co-butylacrylate-co-(2-ethylhexyl)acrylate-co-vinylacetate].

The adhesive layer 3 is present on the sides and above the matrix layer 2 between the cover layer 4 and the protective layer 1. The adhesive layer 3 may be an acrylic copolymer having hydroxyl functional groups. For example, the adhesive layer 3 may be an acrylate-vinylacetate copolymer having hydroxyl functional groups that is crosslinked. The adhesive layer 3 may be a self-curing pressure sensitive adhesive. The acrylic copolymer may be poly[(2-ethylhexyl)acrylate-co-vinylacetate-co-(2-hydroxyethyl)acrylate-co-(2,3-epoxypropyl)methacrylate] or poly[(2-ethylhexyl)acrylate-co-vinylacetate-co-(2-hydroxy-ethyl)acrylate].

The adhesive layer 3 provides sufficient adhesive strength when applied to the user's skin. Although the adhesive layer 3 provides sufficient adhesive strength over the entire period of application (typically up to 7 days), the adhesive layer 3 also allows the transdermal patch to be easily removed from the skin surface at the end of the application, preferably without leaving any residue of the matrix layer 2 and/or the adhesive layer 3 on the skin in the region of the edge of the transdermal patch.

The acrylic copolymer of the adhesive layer may be prepared using one or more monomers selected from the group consisting of acrylic acid, methacrylic acid, acrylic acid esters (in particular alkyl acrylates), methacrylic acid esters (especially alkyl methacrylates), and other unsaturated monomers. (Meth)acrylates preferably have straight-chain or branched alkyl groups of 1 to 12 carbon atoms. Acrylic acid esters may preferably be methyl acrylate, ethyl acrylate, propyl acrylate, butyl acrylate, 2-ethylhexyl acrylate, glycidyl acrylate, and 2-hydroxyethyl acrylate. Methacrylic acid esters may preferably be methyl methacrylate, 2-ethylhexyl methacrylate, glycidyl methacrylate, and 2-hydroxyethyl methacrylate. Other preferred unsaturated monomers are selected from the group consisting of vinyl acetate, vinyl propionate, dibutyl maleate, octylacrylamide, dimethylacrylamide, dimethylaminoethyl acrylate, hydroxyethyl acrylate, hydroxypropyl acrylate, methoxyethyl acrylate, methoxyethyl methacrylate and acrylonitrile, in particular vinyl acetate.

In order to crosslink the acrylic copolymer, the mixture may include suitable crosslinking agents.

The acrylic copolymer may comprise a combination of one or more of the following monomers: 2-ethylhexyl acrylate, glycidyl methacrylate (i.e., 2,3-epoxypropyl methacrylate), 2-hydroxyethyl acrylate, and vinyl acetate. The acrylic copolymer preferably comprises all of these monomers or alternatively a combination of 2-ethylhexyl acrylate, 2-hydroxyethyl acrylate, and vinyl acetate.

Suitable acrylic copolymers of the adhesive layer 3 that are commercially available include DURO-TAK® 87-2516 or 387-2516, DURO-TAK® 87-2287 or 387-2287, DURO-TAK® 87-4287, DURO-TAK® 87-2510 or 387-2510, and GELVA GMS 788 from Henkel Corporation, Bridgewater, N.J., USA. Particularly suitable acrylic copolymers are DURO-TAK® 87-2516 or 387-2516, DURO-TAK® 87-2287 or 387-2287, and DURO-TAK® 87-4287. The polymers are already pre-dissolved in organic solvents and can be used in the adhesive layer 3 without further preparation.

The adhesive layer 3 is a pressure-sensitive adhesive layer on the skin that has sufficient adhesive force over the application period of the transdermal patch. In addition to the acrylic copolymers described above, the adhesive layer 3 may also include one or more conventional self-adhesive (preferably pressure-sensitive) adhesives such as polyacrylates, polyisobutylenes, and polysiloxanes, and/or one or more conventional adhesive substances such as rosin esters and hydrocarbon resins. Preferably, the adhesive layer only includes the acrylic copolymers described above.

The area of the laminate comprising the cover layer 4 and the adhesive layer 3 may be larger than the area of the laminate comprising the protective layer 1 and the buprenorphine-containing matrix layer 2. In the alternative, the area of the laminate comprising the cover layer 4 and the adhesive layer 3 may be the same size as the area of the laminate comprising the protective layer 1 and the buprenorphine-containing matrix layer 2.

Figure 2:
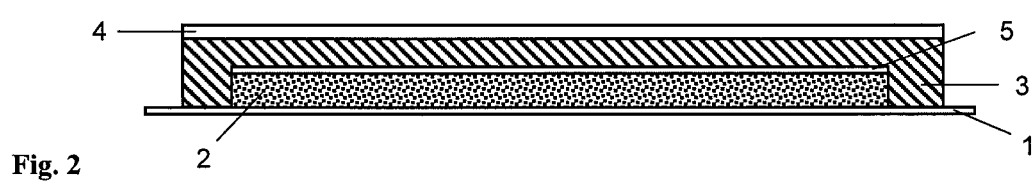
FIG. 2 is a schematic cross-sectional view of a transdermal therapeutic system of the present invention with a protective layer 1, a matrix layer 2, an adhesive layer 3, a cover layer 4, and a separating layer 5 disposed between the matrix layer 2 and the adhesive layer 3.

In a preferred embodiment, the adhesive layer 3 does not comprise buprenorphine in the preparation. During storage, however, buprenorphine can diffuse into the adhesive layer 3 from the matrix layer 2. To minimize or prevent this diffusion process, the transdermal patch may preferably include a separating layer 5 as shown in FIG. 2. The separating layer 5 is preferably arranged between the matrix layer 2 and the adhesive layer 3.

In one embodiment, the transdermal patch is characterized in that the matrix layer 2 is arranged to be in contact with the protective layer 1 and in contact with the adhesive layer 3 but not in contact with the cover layer 4. The adhesive layer 3 is arranged to be in contact with the cover layer 4 and optionally in contact with the protective layer 1. In this embodiment, the separating layer 5 is preferably arranged between the matrix layer 2 and the adhesive layer 3.

As the separating layer 5 of the transdermal patch, any material that is typically used for a separating layer of a transdermal patch may be used. The separating layer 5 may also comprise polyester (e.g., PET). Commercially available products to use as the separating layer 5 include Hostaphan® RN DMF 23 (manufactured by Mitsubishi Polyester Film (Wiesbaden, Germany)) or Grade 0.6 CL PET (manufactured by Loparex (Hammond, Wis., USA)). The thickness of the separating layer may be 10 to 125 microns.

Despite the excellent bond strength, the transdermal patch is preferably easily removed from the skin at the end of the application (usually after up to 7 days). The transdermal patch is also preferably removed without leaving any residue of the matrix layer 2 and/or the adhesive layer 3 on the skin in the region of the edge of the transdermal patch.

As noted above, the transdermal patch preferably contains buprenorphine in the matrix layer 2. Usual buprenorphine-containing matrix layers for transdermal patches are known from EP 0430019 A2, EP 0535111 A1, WO 96/19975 A1, WO 98/36728 A2, EP 2272507 A1, and WO 2012/65740 A1, wherein each of the disclosures on the buprenorphine-containing matrix layers is incorporated by reference into the present application.

Other than a physiologically effective amount of buprenorphine, the matrix layer 2 may include a pressure-sensitive adhesive. The pressure-sensitive adhesives may be the same ones as described above for the adhesive layer 3.

The percentage by weight of buprenorphine, based on the total weight of the matrix layer 2 may be between 1% and 40%, preferably between 5% and 20%, particularly preferably at 10%. The matrix layer 2 of the transdermal patch may comprise a sufficient amount of buprenorphine so that the transdermal patch on the skin of a subject provides from 1 to 100 micrograms (μg) per hour (hr). Specifically, the transdermal patch may provide 5, 7.5, 10, 15, 20, 25, 30, 35, 40, 52.5, 70, or 90 μg/hr of buprenorphine to the skin for a period of at least 72 hours and up to 7 days. The matrix layer 2 of the transdermal patch may comprise 1 to 100 mg of buprenorphine. Specifically, the matrix layer 2 may comprise 5, 7.5, 10, 15, 20, 25, 30, 35, 40, 52.5, 70, or 90 mg of buprenorphine.

The matrix layer 2 optionally includes one or more physiologically appropriate pharmaceutical excipients. The pharmaceutical excipients may be glycols, oils and fats, urea derivatives, saturated or unsaturated fatty alcohols or fatty acids having 8 to 18 carbon atoms or esters thereof, monoglycerides, diglycerides, triglycerides and/or terpenes, tackifiers, softeners, emulsifiers, co-solvents and/or stabilizers.

In one embodiment, the matrix layer 2 includes 1-10 wt % buprenorphine, 10-15 wt % levulinic acid, 10-15 wt % oleyl oleate, 0-10 wt % povidone (polyvinylpyrrolidone) K90, and 50-70 wt % self-adhesive acrylate copolymer based on the total weight of the matrix layer 2. More specifically, the matrix layer 2 may include 10 wt % buprenorphine, 10 wt % levulinic acid, 15 wt % oleyl oleate, 10 wt % povidone (polyvinylpyrrolidone) K90, and 55 wt % pressure-sensitive, self-adhesive acrylate-vinyl acetate copolymer (DURO-TAK® 387-2054) based on the total weight of the matrix layer 2.

The matrix layer 2 and the adhesive layer 3 may have conventional basis weights. For example, the basis weights of the matrix layer 2 and the adhesive layer 3 may be 30 g/m$^2$ to 120 g/m$^2$, preferably 60 g/m$^2$ to 120 g/m$^2$. The matrix layer 2 and the adhesive layer 3 do not need to have the same basis weight. The basis weight of the matrix layer 2 may be 60 g/m$^2$ to 100 g/m$^2$, preferably 80 g/m$^2$. The basis weight of the adhesive layer 3 may be 60 g/m$^2$ to 120 g/m$^2$, preferably 100 g/m$^2$.

For the transdermal patch, conventional patch shapes and patch sizes can be used. In a preferred embodiment, the transdermal patch is rectangular, preferably with one or more rounded corners. The patch size may be 80 cm$^2$ or less. Preferably, the patch size is 5-60 cm$^2$. Specifically, the patch size may be 6.25, 9.38, 12.5, 18.75, 25, 31.25, 37.5, or 50 cm$^2$.

Another embodiment of the present invention is directed to a process for producing a transdermal patch. The configurations and the components of the transdermal patch described above are also applicable to this embodiment of the present invention.

One process for producing the transdermal patch includes the steps of:
producing a laminate comprising a buprenorphine-containing matrix layer 2, a separating layer 5, and a protective layer 1, preparing a laminate comprising an adhesive layer 3, which includes an acrylic copolymer having hydroxyl functional groups, and a cover layer 4 being at least partially bi-elastic, and optionally comprising an interim protective layer on the surface of the adhesive layer 3, optionally removing the interim protective layer of the laminate from step ii) and connecting the laminate of step ii) with the laminate of step i), wherein the separation layer 5 between the adhesive layer 3 and the matrix layer 2 is arranged so that the transdermal patch is produced as shown in FIG. 2, and optionally cutting the transdermal patch into single doses, preferably by suitable punching of the individual patches.

The above-described preferred manufacturing method may alternatively be modified so that a laminate having the matrix layer is prepared, which has no separating layer 5, so that the transdermal patch is produced as shown in FIG. 1. This process can be particularly preferred when the diffusion of buprenorphine into the adhesive layer 3 is expected to be negligible or low.

The third aspect of the present invention relates to methods for the treatment, alleviation, and/or prophylaxis of pain using the patch of the invention. The preferred embodiments of the invention in terms of the components of the transdermal patch described above or the production process described above are also applicable to this embodiment of the present invention.

The fourth embodiment of the present invention relates to a method for the treatment, alleviation, and/or prophylaxis of pain by administering the transdermal patch described above to a subject, preferably human or animal, suffering from pain. The preferred embodiments of the invention in terms of the components of the transdermal patch described above or the production process described above are also applicable to this embodiment of the present invention.

The present invention will hereinafter be described with reference to exemplary embodiments, which are written to be understood only as examples and are not intended to limit the scope of the present application.

EXAMPLES

Part A: Preparation Processes for Transdermal Patches

Preparation Example 1: Preparation of a Laminate Comprising the Matrix Layer 2 with a Physiologically Effective Amount of Buprenorphine Buprenorphine-containing matrices for transdermal patches are disclosed in EP 0430019 A2, WO 96/19975, and WO 98/36728.

1.1 Preparation of a Laminate Comprising the Protective Layer 1, the buprenorphine-Containing Matrix Layer 2, and the Separating Layer 5 in Accordance with Example 1 of EP 0430019

10.0 g each of glutaric acid monomethyl ester, methanol, and butanone, and 15.0 g of 1-dodecanol are mixed under stirring. Subsequently, 10.0 g of buprenorphine base are added. The mixture is stirred until the solid substance is completely dissolved (approximately 30 min, visual inspection). After stirring, 133.0 g of a self-crosslinking acrylate copolymer of 2-ethylhexyl acrylate, vinyl acetate, and acrylic acid 46% in a solvent mixture (ethyl acetate:heptane: isopropanol:toluene:acetyl acetone 37:26:26:4:1) are added. Homogenization follows. After stirring, 1.3 g aluminium acetylacetonate are additionally added and stirred for 3 hours at room temperature. The evaporation loss is compensated. 189.3 g of 52.8% (w/w) drug-containing matrix solution is obtained, which is spread on an aluminized and siliconized polyethylene foil (i.e., protective layer 1) with a 350 micron coating bar. The solvents are removed by drying for 30 minutes at 60° C. Subsequently, the thus obtained matrix layer 2 is laminated with a polyester film of 15 µm thickness (i.e., separating layer 5). Thus, a triple-layer laminate is obtained. The polyester film could also be an interim protective layer to obtain a final patch according to FIG. 1 without a separating layer.

1.2 Preparation of a Laminate Comprising the Protective Layer 1, the Buprenorphine-Containing Matrix Layer 2, and the Separating Layer 5 in Accordance with Example 1 of WO 96/19975 A1 and WO 98/36728 A2

1.139 g of a 47.83 wt % polyacrylate solution with a self-crosslinked acrylate copolymer of 2-ethylhexyl acrylate, vinyl acetate, acrylic acid (solvent:ethyl acetate:heptane:isopropanol:toluene:acetyl acetonate in the ratio of 37:26:26:4:1), 100 g of levulinic acid, 150 g of oleyl oleate, 100 g polyvinylpyrrolidone, 150 g of ethanol, 200 g of ethyl acetate, and 100 g of buprenorphine base are homogenized. The mixture is stirred for about 2 hours and then examined visually to determine if all of the solids are dissolved. Thereafter, the mixture is applied to a siliconized polyester film (i.e., protective layer 1) in such a manner that the mass per unit area of the dried layer of the paste is 80 g per m². The solvents are removed by drying with heated air which is guided over the moist web. Subsequently, the thus obtained matrix layer 2 is laminated with a polyester film of 15 µm thickness (i.e., separating layer 5). Thus, a triple-layer laminate is obtained. The polyester film could also be an interim protective layer to obtain a final patch according to FIG. 1 without a separating layer.

In a preferred embodiment of the present invention, a crosslinkable acrylate-vinyl acetate copolymer with hydroxyl and/or carboxyl functional groups is used as the acrylate copolymer of Preparation Examples 1.1 and 1.2. Another example of a crosslinkable acrylate-vinyl acetate copolymer having carboxyl functional groups is poly [acrylic acid-co-butyl acrylate-co-(2-ethylhexyl)acrylate-vinyl acetate]. A commercially available product is DURO-TAK® 87-2054 or 387-2054 from Henkel Corporation (Bridgewater, N.J., USA). The matrix layer 2 preferably has a basis weight of 80 g/m².

The individual characteristics of Preparation Examples 1.1 and 1.2 and their alternatives may be used alone or combined with other features of the general description of the present invention.

Preparation Example 2

Preparation of a Laminate Comprising the Cover Layer 4, which is at Least Partially Bi-Elastic, and the Adhesive Layer 3, which Includes an Acrylic Copolymer Having Hydroxyl Functional Groups The acrylate adhesive solution is cast at four (4) inches to a defined thickness onto a siliconized interim protective layer (silicone coated PET release liner, Grade 29058 D3.0 Clear PET×X5000A/000, available from Loparex, Iowa City, Iowa, USA) to obtain a coat weight of the adhesive layer 3 of 64.5±6.5 mg/in² (equivalent to 100 g/m²). The coated release liner is conveyed through an oven equipped with two temperature-controlled zones which removes the solvent (dwell time: between 7.5 and 15 min). When the material exits the oven, a bi-elastic cover layer 4 (KOB No. 053, available from KOB—Karl Otto Braun KG, Wolfenstein, Germany) is introduced to the dried adhesive matrix and laminated utilizing a nip roll (with a pressure at 40 PSI) to obtain a three layer laminate.

The above mentioned process was used to prepare laminates comprising DURO-TAK® 87-4287 (2a), DURO-TAK® 387-2287 (2b) and DURO-TAK® 387-2516 (2c) as acrylic copolymers having hydroxyl functional groups.

The individual characteristics of Preparation Example 2 and its alternatives may be used alone or combined with other features of the general description of the present invention.

Comparative Preparation Example 3

Preparation of Laminate Comprising the Cover Layer 4, which is at Least Partially Bi-Elastic, and an Adhesive Layer, which Includes an Acrylic Copolymer with Carboxylate Functional Groups Rather than Hydroxyl Functional Groups The acrylate adhesive solution (DURO-TAK® 87-2051) is cast at four (4) inches to a defined thickness onto a siliconized interim protective layer (silicone coated PET release liner, Grade 29058 D3.0 Clear PETxX5000A/000, available from Loparex, Iowa City, Iowa, USA) to obtain a coat weight of the adhesive layer 3 of 64.5±6.5 mg/in$^2$ (equivalent to 100 g/m$^2$). The coated release liner is conveyed through an oven equipped with two temperature-controlled zones which removes the solvent (dwell time: 7.5 min). When the material exits the oven, a bi-elastic cover layer 4 (KOB No. 053, available from KOB—Karl Otto Braun KG, Wolfenstein, Germany) is introduced to the dried adhesive matrix and laminated utilizing a nip roll (with a pressure at 40 PSI) to obtain a three layer laminate.

Preparation Example 4

Preparation of Transdermal Patches

The interim protection layer is removed from the second laminate produced by Preparation Example 2 and Comparative Preparation Example 3. Then, the second laminate is laminated to the first laminate as shown in FIG. 2 to produce inventive and comparative transdermal patches. The area of the laminate comprising the cover layer 4 and the adhesive layer 3 is larger than the area of the laminate comprising the protective layer 1 and buprenorphine-containing matrix layer 2 so that the adhesive layer 3 is present on all sides of the matrix layer 2 that is not laminated to the protective layer 1 while the separating layer 5 completely covers the top of the matrix layer 2 (see FIG. 2). As such, the inventive transdermal patch comprises a drug-containing surface (i.e., the surface of the laminate comprising the protective layer 1, the buprenorphine-containing matrix layer 2, and the separating layer 5) of 25 cm$^2$ and a non-drug-containing surface (i.e., the surface of the laminate comprising the cover layer 4 and the adhesive layer 3) of 52 cm$^2$. However, each surface can have a range of sizes. For example, the drug-containing surface may be 6.25 cm$^2$ to 50 cm$^2$, and the non-drug-containing surface may be 21 cm$^2$ to 88 cm$^2$.

The individual characteristics of Preparation Example 4 and its alternatives may be used alone or combined with other features of the general description of the present invention.

Part B:

180° Release Liner Peel Test

The three layer laminates obtained in Preparation Examples 2a, 2b, and 2c and Comparative Preparation Example 3 are slit into rolls of a width of 50 mm. The rolls are stored in airtight, heat sealed foil bags and held at accelerated conditions (40° C. and 75% RH) until measurement.

This test measures the force required to separate the release liner from the adhesive layer of the test sample. Samples held at accelerated conditions are removed from the chamber and are allowed to condition at room temperature 24 hours prior to test. The sample to be tested is cut using a 24 mm sample cutter to standardize the width (sample size: 50×24 mm). The instrument used to test the force is an Instron Model 5543 fitted with pneumatic clamps. A small portion of the release liner is peeled back and gripped by the lower pneumatic clamp and a portion of the test specimen is gripped by the upper pneumatic clamp. The test article is peeled away from the release liner at a peel angle of 180° and a peel rate of 300 mm/min, and the peel force is recorded. This procedure is repeated using five independent samples. The average of the five tests is reported in Table 1.

TABLE 1

| | 180° Liner Release [gF/24 mm] | | | |
| --- | --- | --- | --- | --- |
| Time point [days] | 2a DURO-TAK ® 87-4287 | 2b DURO-TAK ® 387-2287 | 2c DURO-TAK ® 387-2516 | 3 DURO-TAK ® 387-2051 |
| Initial | 24 | 27 | 22 | 26 |
| 14 | 26 | 30 | 29 | 12 |
| 28 | 29 | 30 | 32 | 0 |

90° Peel Adhesion Test to Stainless Steel

The three layer laminates obtained in Preparation Examples 2a, 2b, and 2c and Comparative Preparation Example 3 are slit into rolls of a width of 50 mm. The rolls are stored in airtight, heat sealed foil bags and held at accelerated conditions (40° C. and 75% RH) until measurement.

This test measures the force required to remove (peel away) a coated adhesive from a polished 316L stainless steel test panel. Samples held at accelerated conditions (40° C. and 75% RH) are removed from the chamber and are allowed to condition at room temperature 24 hours prior to test. The sample to be tested is cut using a 24 mm sample cutter to standardize the width (sample size: 50×24 mm). The release liner is removed, and the adhesive is applied to the stainless steel panel using a 4.5 lb (2045 g) hand roller. The test panel is allowed to sit 2-5 minutes prior to test. The instrument used to test the force is an Instron Model 5543 fitted with pneumatic clamps and a 90° peel fixture. The test panel is attached to the peel fixture and a portion of the test specimen is gripped by the upper pneumatic clamp. The test article is peeled away from the stainless steel panel at a peel angle of 90° and a peel rate of 300 mm/min, and the peel force is recorded. This procedure is repeated using five independent samples. The average of the five tests is reported in Table 2.

TABLE 2

| | 90° Adhesion - Stainless Steel Panels [gF/24 mm] | | | |
|---|---|---|---|---|
| Time point [days] | 2a DURO-TAK® 87-4287 | 2b DURO-TAK® 387-2287 | 2c DURO-TAK® 387-2516 | 3 DURO-TAK® 387-2051 |
| Initial | 834 | 897 | 1119 | 582 |
| 14 | 592 | 534 | 710 | 56 |
| 28 | 519 | 606 | 567 | 0 |

Shrinkage

This test measured the amount of relaxation (shrinkage) the bi-elastic cover layer 4 exhibited after it is cut. Three samples of each three layer laminate, as obtained in Preparation Examples 2a, 2b, and 2c and Comparative Preparation Example 3, were cut (length of the samples: 84 mm, width of the samples: 62-104 mm) and measured in the machine coating direction immediately. The samples were stored open at ambient conditions, and the measurements were repeated at various points over 28 days. All measurements were taken with a ruler approximately 35 mm from the bottom edge of the article under test. Each measurement is divided by the initial measurement and expressed as a percentage. The average of the three test samples is reported in percentage in Table 3.

TABLE 3

| | Shrinkage [%] | | | |
|---|---|---|---|---|
| Time point [days] | 2a DURO-TAK® 87-4287 | 2b DURO-TAK® 387-2287 | 2c DURO-TAK® 387-2516 | 3 DURO-TAK® 387-2051 |
| 1 | 0.4 | 0.7 | 0 | 3.6 |
| 3 | 0.4 | 0.9 | 0 | 4.4 |
| 7 | 0.4 | 1.4 | 0 | 4.4 |
| 14 | 0.4 | 2.3 | 0 | 4.6 |
| 28 | 0.6 | 3.0 | 0.2 | 5.4 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A transdermal patch comprising:
a removable protective layer,
a matrix layer consisting of a single layer which contains a physiologically effective amount of buprenorphine or pharmaceutically acceptable salts thereof,
an adhesive layer, and
a cover layer,
wherein the cover layer is at least partially bi-elastic and the adhesive layer comprises an acrylic copolymer having hydroxyl functional groups, and
wherein the matrix layer is in contact with the removable protective layer.

2. The transdermal patch according to claim 1, wherein the matrix layer is arranged to be in contact with the protective layer and in contact with the adhesive layer but not in contact with the cover layer, and the adhesive layer is arranged to be in contact with the cover layer and is optionally in contact with the protective layer.

3. The transdermal patch according to claim 1, wherein a separating layer is between the matrix layer and the adhesive layer.

4. The transdermal patch according to claim 1, wherein the cover layer has an elasticity in the longitudinal and transverse direction of 20% or more.

5. The transdermal patch according to claim 1, wherein the cover layer has an elasticity in the longitudinal direction of 40-60%.

6. The transdermal patch according to claim 1, wherein the cover layer has an elasticity in the transverse direction of 35% or more.

7. The transdermal patch according to claim 1, wherein the acrylic copolymer having hydroxyl functional groups is crosslinked.

8. The transdermal patch according to claim 1, wherein the acrylic copolymer comprises a combination of 2-ethylhexyl acrylate, glycidyl methacrylate, 2-hydroxyethyl acrylate, and vinyl acetate.

9. The transdermal patch according to claim 1, wherein the acrylic copolymer comprises a combination of 2-ethylhexyl acrylate, 2-hydroxyethyl acrylate, and vinyl acetate.

10. The transdermal patch according to claim 1, wherein the adhesive layer does not comprise buprenorphine.

11. A transdermal patch comprising:
a removable protective layer,
a matrix layer consisting of a single layer which contains a physiologically effective amount of buprenorphine,
an adhesive layer, and
a cover layer,
wherein the cover layer is at least partially bi-elastic and the adhesive layer comprises an acrylic copolymer having hydroxyl functional groups.

12. A method for treating or alleviating pain, comprising:
administering a transdermal patch according to claim 1 to a patient in need thereof.

13. A process for preparing a transdermal patch, comprising the following steps:
providing a composition comprising buprenorphine and producing a buprenorphine-containing matrix layer therefrom,
providing a composition comprising an acrylic copolymer having hydroxyl functional groups and producing an adhesive layer therefrom,
providing a protective layer,
providing a bi-elastic cover layer, and
producing a transdermal patch according to claim 1.

14. A process for producing a transdermal patch according to claim 1, comprising the steps of:
producing a first laminate comprising a buprenorphine-containing matrix layer and a protective layer,
preparing a second laminate comprising an adhesive layer, which includes an acrylic copolymer having hydroxyl functional groups, and a cover layer,
connecting the first laminate comprising the matrix with the second laminate comprising the adhesive layer to produce the transdermal patch.

15. The process according to claim 14, wherein a top surface of the buprenorphine-containing matrix layer is covered with a separating layer.

16. The process according to claim 14, wherein the second laminate comprising the adhesive layer further comprises an interim protective layer on the surface of the adhesive layer, which is removed before connecting the second laminate with the first laminate comprising the matrix.

17. The process according to claim 14, further comprising cutting the transdermal patch into single doses.

* * * * *